(12) United States Patent
Rovati et al.

(10) Patent No.: US 7,465,299 B2
(45) Date of Patent: Dec. 16, 2008

(54) MONITORING OF RETINAL TEMPERATURE DURING LASER THERAPY

(76) Inventors: Luigi Rovati, via Notari 98, 41100 Modean (IT); Giovanni Staurenghi, via Tiraboschi 8, 20135 Milano (IT)

(*) Notice: Subject to any disclaimer, the term of this patent is extended or adjusted under 35 U.S.C. 154(b) by 246 days.

(21) Appl. No.: 11/181,524

(22) Filed: Jul. 14, 2005

(65) Prior Publication Data

US 2006/0084948 A1  Apr. 20, 2006

Related U.S. Application Data

(60) Provisional application No. 60/587,758, filed on Jul. 14, 2004.

(51) Int. Cl.
*A61B 18/18* (2006.01)

(52) U.S. Cl. .............................. 606/4; 606/10; 351/211

(58) Field of Classification Search .................. 606/4–6, 606/10–12; 351/205–219; 128/898
See application file for complete search history.

(56) References Cited

U.S. PATENT DOCUMENTS

| | | | |
|---|---|---|---|
| 5,777,719 A * | 7/1998 | Williams et al. | 351/212 |
| 6,508,812 B1 * | 1/2003 | Williams et al. | 606/5 |
| 6,540,391 B2 | 4/2003 | Lanzetta et al. | |
| 6,684,097 B1 | 1/2004 | Parel et al. | |
| 6,704,588 B2 | 3/2004 | Ansari et al. | |
| 6,830,567 B2 * | 12/2004 | Schuele et al. | 606/4 |
| 7,041,063 B2 * | 5/2006 | Abreu | 600/549 |
| 7,115,120 B2 * | 10/2006 | Lin | 606/4 |
| 2004/0098070 A1 * | 5/2004 | Mohr et al. | 607/89 |

OTHER PUBLICATIONS

Schule et al., "Noninvasive determination of temperature-induced sub-cellular changes in cells using light scattering spectroscopy" presented at SPRC 2003.*
Schule et al., "Noninvasive temperature measurements during laser irradiation of the retina with optoacoustic techniques", SPIE vol. 4611, pp. 64-71, 2002.*
Schule et al., "Noninvasive determination of temperature-induced sub-cellular changes . . . ", presented at SPRC 2003.
Molebny, "Laser microradar technique for eye fundus investigation," SPIE vol. 5086, pp. 229-235, 2003.
Schule et al., "Noninvasive temperature measurements during laser irradiation of the retina . . . ", SPIE vol. 4611, pp. 64-71, 2002.
Maret et al., "Multiple Light Scattering from disordered Media . . . ", Z. Phys. B-Condensed Matter 65, pp. 409-413, 1987.
Boas et al., "Spatially varying dynamical properties of turbid media . . . ", J. Opt. Soc. Am. A, vol. 14, No. 1, pp. 192-215, 1997.
Boas et al., "Scattering and Imaging with Diffusing Temporal . . . ", The American Physical Society, vol. 75, No. 9, pp. 1855-1858, 1995.
Pine et al., "Diffusing-Wave Spectroscopy," The American Physical Society, vol. 60, No. 12, pp. 1134-1137, 1988.
Nilsson et al., "Changes in Spectral Shape of Tissue . . . ", Applied Optics, vol. 37, No. 7, pp. 1256-1267, 1998.

(Continued)

*Primary Examiner*—Ahmed M Farah
(74) *Attorney, Agent, or Firm*—Fay Sharpe LLP

(57) ABSTRACT

In a laser eye treatment apparatus, a probe light source generates a secondary emitted light emanating from a treatment area of retinal tissue that is irradiated by a treatment light source. An optical detector detects the secondary emitted light. A processor statistically analyzes the secondary emitted light to determine a temperature of the treatment area of retinal tissue.

18 Claims, 7 Drawing Sheets

OTHER PUBLICATIONS

Mainster et al., "Transpupillary thermotherapy for age-related macular . . . ", Seminars in Ophthalmology, vol. 16, No. 2, pp. 55-59, 2001.

Kaplan et al., "Light-scattering Microscope," *Applied Optics*, vol. 38, No. 19, pp. 4151-4157, (1999).

Ansari et al., "A Compact Fiber Optic Eye Diagnostic System," *NASA Technical Memorandum* 107099, pp. 1-6, (1996).

Preece et al., "Monte Carlo Modelling of the Spectral Reflectance of the Human Eye," *Phys. Med. Biol.* 47, pp. 2863-2877, (2002).

* cited by examiner

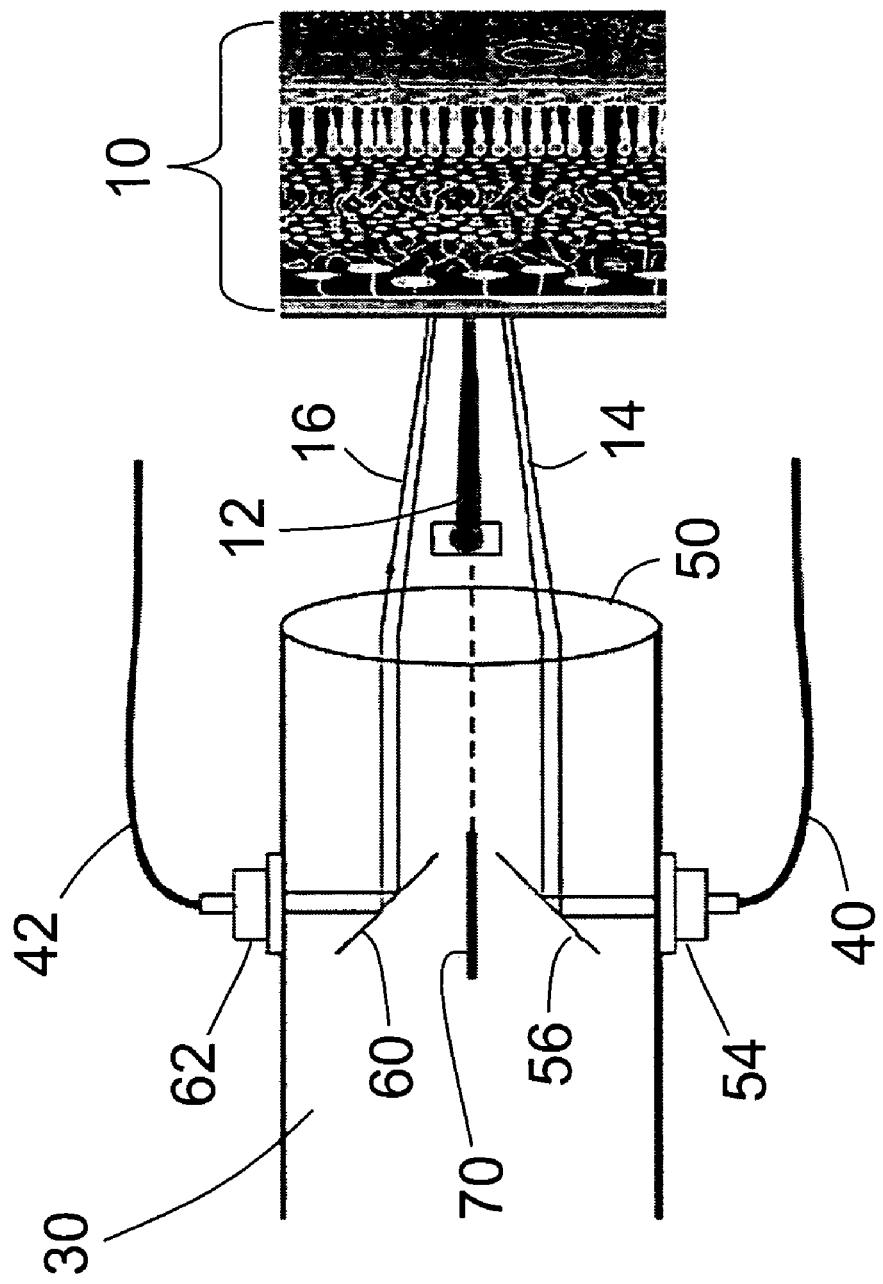

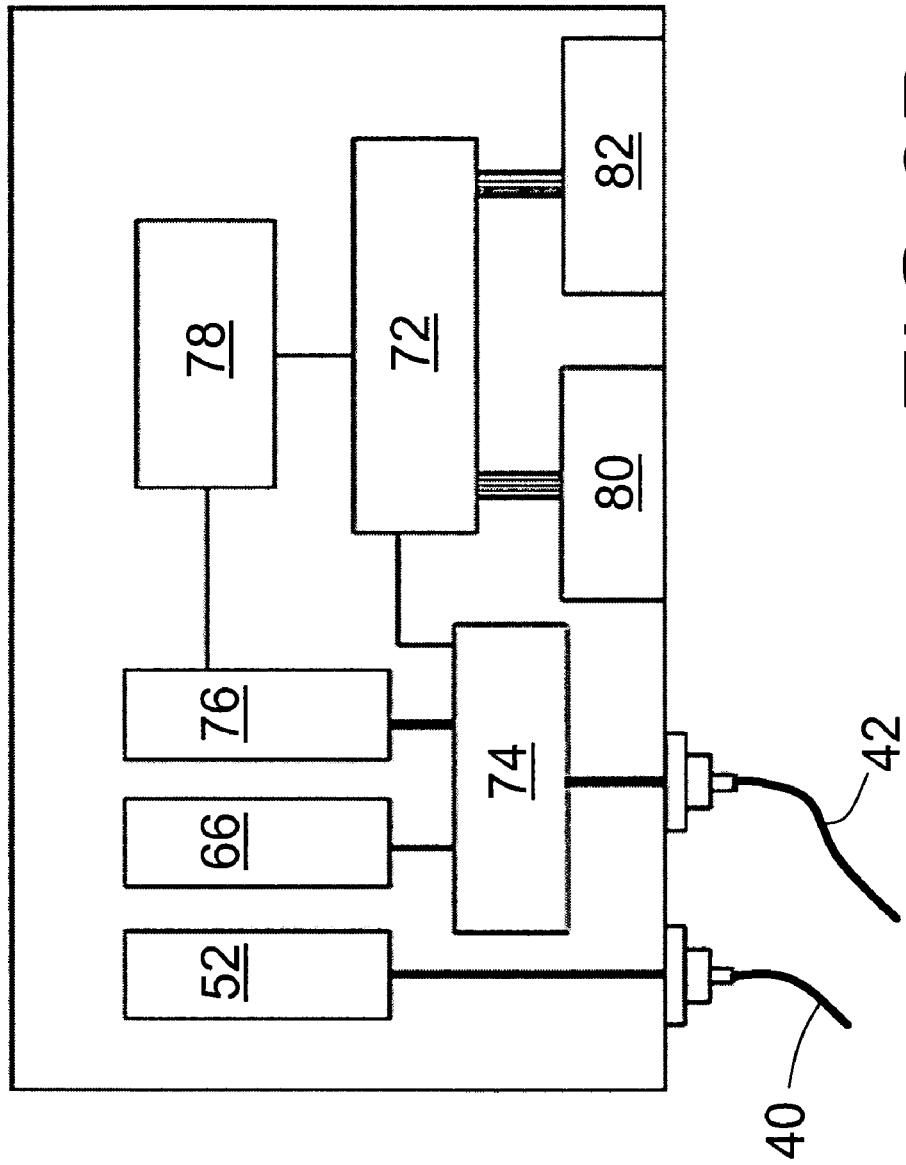

MONITORING OF RETINAL TEMPERATURE DURING LASER THERAPY

BACKGROUND

This application claims the benefit of U.S. Provisional Application No. 60/587,758, filed Jul. 14, 2004. U.S. Provisional Application No. 60/587,758 is incorporated by reference herein in its entirety.

The following relates to the surgical and medical monitoring arts. It especially relates to monitoring of retinal temperature during laser eye surgery, and will be described with particular reference thereto. However, the invention will also find application in conjunction with other optical surgical procedures and in the monitoring of ocular tissue temperature during various ocular medical procedures and clinical ophthalmology studies.

A long-felt need in laser eye therapy is the ability to monitor the temperature of the irradiated tissue during the laser procedure. In ophthalmology laser therapy is used to treat a number of different ocular tissues and ocular pathologies, including retinal tissue and diseases. Age-related macular degeneration, which is a leading cause of poor vision in aged persons, is one pathology that can be treated using laser surgery. When a choroidal neovascularization (CNV) is present, the decrease of vision is typically more rapid and irreversible. Laser treatment allows closure of CNV; however some surrounding retinal tissue is also destroyed. Accurate control of retinal temperature during the laser treatment can reduce damage of healthy tissue during laser eye treatment. For example, one proposed treatment which reduces retinal damage is transpupillary thermotherapy (TTT). Conventional retinal photocoagulation uses brief 40° C. to 60° C. temperature increases to produce lesions that are immediately visible. In comparison, TTT uses lower (10° C.) temperature increases, but maintains them for about 60 seconds to treat CNV. In typical laser eye therapy, these temperatures are estimated based on a mathematical model of the effect of the laser on the retina. Such temperature estimates are approximate, and the actual retinal temperature varies among patients and retinal location of the treatment.

Reported complications or adverse events of TTT for neovascular age-related macular degeneration include retinal pigment epithelial (RPE) tear and retinal arteriole occlusion. Randomized, prospective controlled clinical trials are under way to compare outcomes of TTT intervention for occult CNV with the natural progression of the disease.

The increase in temperature during laser photocoagulation is proportional to retinal irradiance or power density for a particular chorioretinal pigmentation, exposure duration, spot size, and laser photocoagulator wavelength. TTT uses large spot sizes to produce low retinal irradiances and temperature increases. Its sub-threshold nature is potentially a therapeutic advantage. However, it is also a practical disadvantage, because smaller lesions produced by TTT are not readily detectable. Hence, if retinal irradiance is insufficient to produce a therapeutic temperature increase, this may not be readily detected by medical personnel. Evaluating different aspects of the effect of thermal damage on the RPE and neural retina could improve the reproducibility of sub-threshold photocoagulation results.

Retinal tissue temperature can be monitored by either non-invasive or invasive techniques. Non-invasive techniques include computationally estimating the temperature using proper mathematical models, or employing x-ray or nuclear magnetic resonance (NMR) instrumentation.

Existing commercial instrumentation typically employs mathematical modeling, and calculates the retinal temperature during treatment using a simple model [see, e.g., Mainster et al., *Transpupillary thermotherapy for age-related macular degeneration: principles and techniques*, Semin. Ophthalmol. Vol. 16 no. 2, pp. 55-59 (2001).] In performing laser eye therapy, in some cases several treatment parameters are adjusted based on the experience and knowledge of the surgeon, technician, or other medical operator. These approaches suffer from substantial inter-subject and intra-subject variability.

Analysis of the images obtained by x-ray and NMR techniques provide a measure of the temperature of the irradiated ocular tissue [see, e.g., Parel et al., U.S. Pat. No. 6,684,097, January 2004]. However the required instrumentation is expensive and may present risks to the patient.

Optical techniques have potential advantages as compared with techniques such as mathematical modeling or characterization by x-ray or NMR. Optical techniques have the potential to perform direct temperature measurement of retinal tissue close to the laser-treated area.

Efforts have been made to use optical methods to measure the retinal temperature during laser treatment. The systems so far proposed include: (i) the optoacoustic techniques; (ii) low coherence interferometry techniques; (iii) interferometric techniques; and (iv) spectral analysis of backscattered light. However, these existing optical techniques typically do not provide a robust, accurate, and reliable determination of the end point of laser treatment that is suitable for use in conjunction with clinical laser eye treatment.

Optoacoustic methods are discussed in Shoule et al., *Non-invasive temperature measurements during laser irradiation of the retina with optoacoustic techniques*, Proc. SPIE Vol. 4611, pp. 64-71 (2002). In the technique there disclosed, laser-induced pressure waves are generated by interaction of laser irradiation with retinal tissue. A maximum peak of the pressure is proportional to the laser intensity and under certain conditions depends on the temperature of the irradiated tissue. The technique is invasive insofar as an acoustic transducer is placed in physical contact with the patient's eye. The transducer can be integrated into a contact lens which is used in the therapy. However, different contact lenses are used for different procedures and/or patients, and the acoustic transducer should be optimized as a function of lens characteristics. Yet another disadvantage is that precise calibration is required for each specific lens-transducer configuration.

Low-coherence interferometry techniques have been proposed by Lanzetta et al., U.S. Pat. No. 6,540,391, April 2003, for recording lesion formation during ocular laser photocoagulation. This technique does not directly measure retinal temperature, but rather detects morphological changes induced in response to the interaction of ocular tissue with the laser beam. Another interferometric approach is disclosed in Vasyl Molebny, Proc. SPIE vol. 5086, pp. 229-35 (2003). This technique also does not directly measure retinal temperature, but rather measures topological tissue changes during tissue heating. The increase in temperature of the irradiated ocular tissue leads to dimensional changes, and thus to the changes in the topography of eye bottom that can be detected by a double-beam interferometric technique. Such topological changes are expected to be small, however, and moreover correlating such dimensional changes with retinal temperature may be difficult.

Spectral analysis of scattered light has been used to monitor heat-induced sub-cellular structural changes of a human retina, as disclosed in Schuele et al., *Noninvasive determination of temperature-induced sub-cellular changes in RPE* using light scattering spectroscopy, presented at the SPIE conf. 2004 Photonics West, PW04B-BO11-50. Results were observed in-vitro on single layer of human retinal pigment epithelial (RPE) cells on a glass slide. Strong spectral changes of the backscattered light with temperature were observed for temperature changes of around 25-50° C. This method may be susceptible to inter-subject variability induced by differences in pigmentation between subjects. Moreover, changes in the tissue vascularization could also induce spectral changes in the backscattered light which are unrelated to retinal temperature.

The present disclosure provides improved apparatuses and methods that overcome the above-mentioned limitations and others.

BRIEF SUMMARY

According to one aspect, a method is provided for measuring retinal temperature. Secondary emitted light is generated emanating from retinal tissue. The secondary emitted light is statistically analyzed to determine the temperature of the retinal tissue.

According to another aspect, a laser eye treatment method is provided. A treatment laser is applied to a treatment area of retinal tissue. Secondary emitted light is generated emanating from the treatment area of retinal tissue. The secondary emitted light is statistically analyzed to determine a temperature of the treatment area of retinal tissue.

According to yet another aspect, a laser eye treatment apparatus is disclosed. A probe light source generates secondary emitted light emanating from a treatment area of retinal tissue that is irradiated by a treatment light source. An optical detector detects the secondary emitted light. A processor statistically analyzes the secondary emitted light to determine the temperature of the treatment area of retinal tissue.

Numerous advantages and benefits of the present invention will become apparent to those of ordinary skill in the art upon reading and understanding the present specification.

BRIEF DESCRIPTION OF THE DRAWINGS

The invention may take form in various components and arrangements of components, and in various process operations and arrangements of process operations. The drawings are only for purposes of illustrating preferred embodiments and are not to be construed as limiting the invention. In the drawings, layer thicknesses, optical paths, and other dimensions are not drawn to scale.

FIG. 3A diagrammatically shows the optical components of the measurement system of FIG. 2.

FIG. 3B shows a block diagram of the control unit of the measurement system of FIG. 2.

DETAILED DESCRIPTION OF PREFERRED EMBODIMENTS

Figure 1:
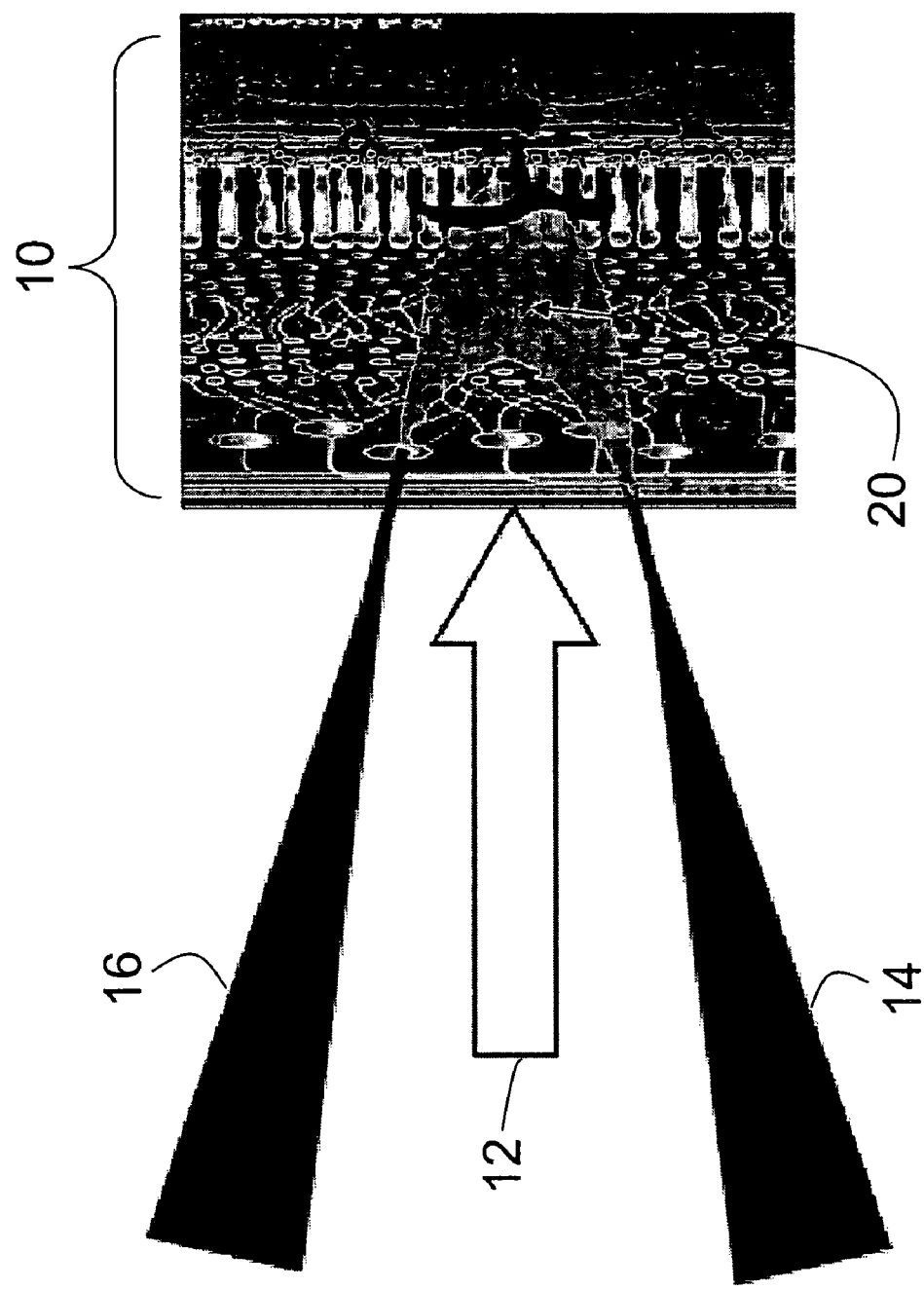
FIG. 1 diagrammatically shows measurement of retinal tissue temperature by measuring scattered light produced by a low power probe beam.

With reference to FIG. 1, the optical techniques disclosed herein exploit temporal fluctuation of secondary emitted photons from the irradiated tissue to measure the tissue temperature. Retinal tissue 10 is treated using a treatment laser beam 12. The tissue is also illuminated by a low power probe beam 14 illuminating the retinal tissue 10 at an angle respective to the treatment laser beam 12. In some embodiments, the probe beam 14 is a focused laser beam; however, focused lamp light, focused light from a semiconductor light emitting diode (LED) or laser, or the like can also be used. Interaction of the probe beam 14 with the retinal tissue 10 produces a secondary beam 16 of light that is collected angularly symmetrically with respect to the treatment laser beam 12. The temperature of the treated retinal region 10 is determined by analyzing the scattering properties of a zone 20 included within the probe beam 14 and from which the secondary radiation 16 is emitted. In some contemplated embodiments, the treatment laser beam 12 generates the secondary beam, in which case the low power probe beam 14 is suitably omitted.

Absorption and scattering are generally the predominant phenomena governing photons propagating through the retinal tissue 10. Absorption effects are described by the absorption coefficient $\mu_a$. Scattering is the dominant photon-tissue interaction at near infra-red (NIR) wavelengths in the range of about 700 nanometers to 1000 nanometers. When a photon is scattered, the collision is typically substantially elastic, and the new direction in which the scattered photon travels depends upon the photon energy, i.e. wavelength, and upon the size, shape and relative refractive index of the scattering molecules. Scattering effects are described by the reduced scattering or transport scattering coefficient $\mu'_s(\lambda)=(1-g)\mu_s(\lambda)$, where: $\mu_s(\lambda)$ is the reciprocal of the mean distance between scattering events; and g is the mean cosine of the scattering angle or scattering phase function.

With continuing reference to FIG. 1, the retinal tissue 10 is a mixture of macromolecules, such as haemoglobine, retina pigment epithelum (RPE), photoreceptors, intephotoreceptor matrix (IPM), which contains proteins, glycoproteins, and proteoglycans, ganglion cells, nerve fiber cells, and so forth. Some of these molecules are rigidly fixed into the structural matrix of the retina, whereas others can move. The motion of these molecules depends on various parameters, such as shape and size of the molecules, interaction among other molecules, constraints due to membranes, and so forth. The motion is induced by blood flow and by the temperature. Temperature-induced motion of the molecules is typically in the form of Brownian motion, and is suitably described by a diffusion coefficient $D_B$ of the colloid. The diffusion coefficient $D_B$ is generally proportional to the average temperature of the retinal tissue 10. Movement of molecules in the retinal tissue 10 induces a fluctuation in the number of secondary emitted photons in the secondary beam 16. By analyzing the signal fluctuations, the retinal tissue temperature determined therefrom.

Fluctuations of the secondary emitted beam 16 are suitably characterized by computing the normalized intensity autocorrelation function, which is defined as:

$$g_2(r, \tau) = \frac{\langle I(r, t) \cdot I(r, t + \tau) \rangle}{\langle I(r, t) \rangle^2}, \qquad (1)$$

where $I(r,t)$ is the diffuse light intensity detected at distance r from the probe beam 14 at time t, and the angle brackets < > denote the time average. For an ergotic system, the diffuse light electric field autocorrelation function $G_1(r,\tau)$ is derived using the Siegert relation [see, e.g., B. Chu, *Laser Light Scattering*, Academic Press, New York (1974)]:

$$g_2(r, \tau) = 1 + \beta \frac{|G_1(r, \tau)|}{\langle I(r, t) \rangle^2}, \qquad (2)$$

where $\beta$ represents the coherence factor. In an ideal scattering system, the coherence factor $\beta$ is equal to 1.

In one suitable embodiment, the retinal tissue 10 is modeled as a turbid semi-infinite homogeneous medium illuminated with a continuous-wave pencil-light source, which can be described by a diffuse equation [see, e.g., G. Maret et al., *Multiple light scattering from disordered media—The effect of Brownian motion of scatterers*, Z. Phys. B 65, pp. 409-13 (1987); D. J. Pine et al., *Diffusing-wave spectroscopy*, Phys. Rev. Lett. 60, pp. 1134-37 (1988); D. A. Boas et al., *Scattering and imaging with diffusing temporal field correlations*, Phys. Rev. Lett. 75, pp. 1855-58 (1995)].

A light electric field autocorrelation function satisfies this diffusion equation [see, e.g., D. A. Boas et al., *Scattering and imaging with diffusing temporal field correlations*, Phys. Rev. Lett. 75, 1855-58 (1995); D. A. Boas et al., *Spatially varying dynamical properties of turbid media probed with diffusing temporal light correlation*, J. Opt. Soc. Am. A, vol. 14, no. 1, pp. 192-215 (1997)], thus yielding:

$$\left( -\frac{1}{3\mu'_s} \nabla^2 + \frac{1}{3} \alpha \mu'_s k_o^2 \langle \Delta r^2(\tau) \rangle \right) \cdot G_1(r, t) = S_o \delta(r - r_s), \qquad (3)$$

where $k_o$ is the wavenumber of the light in the retinal tissue 10, $\langle \Delta r^2(\tau) \rangle$ is the mean squared displacement of the molecules over a time interval t, and $\alpha$ is the probability that the photon event is due to a moving molecule or molecules. $S_o$ and $r_s$ represent constants related to the power and the position of the probe beam 14, respectively.

In some embodiments, the motion of the illuminated molecules is modeled as being substantially Brownian, and the retina capillary network is approximated as a random flow parameterized by a Brownian model. In this approximation, the analytical solution of Equation (3) is given by:

$$G_1(\rho, \tau) = \frac{3\mu'_s}{4\pi} \left( \frac{\exp(-k_D r_1)}{r_1} - \frac{\exp(-k_D r_2)}{r_2} \right). \qquad (4)$$

See, e.g., D. A. Boas, *Diffuse photon probes of structural and dynamical properties of turbid media: theory and biomedical applications*, Ph.D. dissertation (Department of Physics and Astronomy, University of Pennsylvania, Philadelphia, Pa., 1996). In Equation (4), $\rho$ is the distance between the position of the probe beam and the collection point, the parameters $r_1$ and $r_2$ are given by:

$$r_1 = \sqrt{\rho^2 + \frac{1}{\mu'_s + \mu_a}} \; ; \; r_2 = \sqrt{\rho^2 + \left( \frac{1}{\mu'_s + \mu_a} + 2\frac{1.76}{\mu'_s} \right)^2}, \qquad (5)$$

and the parameter $k_D$ is defined by:

$$k_D^2 = 3\mu'_s \mu_a + 6\mu'^2_s k_o^2 \alpha D_B \tau = k_{D0}^2 + k_{D1}^2 \tau \qquad (6).$$

Average absorption and scattering coefficients of the retinal tissue 10 are reported in literature.

In one approach for clinical retinal temperature measurement, absorption and scattering coefficients and parameter $\alpha D_B$ is taken as substantially proportional to temperature. Thus $k_{D1} = K_{cal} T$, where $K_{cal}$ is a calibration constant, T is the retinal temperature at the point under test, and $k_{D0}$ represent the part of $k_D$ that is not temperature-dependent calculated as:

$$k_{D0} = \lim_{T \to 0} \sqrt{3\mu'_s \mu_a}. \qquad (7)$$

This limit can be evaluated according to data reported in literature. See, e.g. Nilsson, A M, Sturesson, C, Liu, D L, and Andersson-Engels, S. 1998. Changes in spectral shape of tissue optical properties in conjunction with laser-induced thermotherapy. Appl. Opt., 37(7), 1256-1267.

To determine the calibration constant $K_{cal}$, measurements are performed before the laser eye treatment is commenced. At this time, the retinal temperature is about equal to the body temperature, i.e., about 37° C. The normalized intensity autocorrelation function $g_2(\tau)$ is measured, and the electric field autocorrelation $G_1$ is calculated using Equation (2). Using a non-linear fit algorithm or other algorithm, an optimal $k_D$ value is determined that substantially fits this electric field autocorrelation function $G_1$ calculated from Equation (2) with its theoretical trend expressed by Equation (4). From this determined value of $k_D$ and using Equation (6) $k_{D1}$ is calculated. The calibration constant $K_{cal}$ is then given as $K_{cal} = k_{D1}/T$ where T=37° C. for this measurement performed before commencing laser eye treatment. More complex models for the relationship between $k_{D1}$ and the retinal temperature can be employed. For example, a linear relationship including an intercept can be used, with the intercept being determined from a linear relationship between the retinal temperature and $k_{D1}$.

During the laser eye treatment, the retinal temperature is evaluated as follows. The normalized intensity autocorrelation function $g_2(\tau)$ is measured periodically, for example once per second. The electric field autocorrelation $G_1$ is calculated using Equation (2). Using a non-linear fit algorithm or other algorithm, an optimal $k_D$ value is determined that substantially fits this electric field autocorrelation function $G_1$ with its theoretical trend expressed by Equation (4). From this determined value of $k_D$ and using Equation (6) $k_{D1}$ is calculated. The retinal temperature is calculated from $k_{D1}$ according to $T = k_{D1}/K_{cal}$, where $K_{cal}$ was calculated in the calibration measurement performed prior to commencing laser eye treatment. The retinal temperature T is displayed or otherwise communicated to the person performing the laser treatment. The process is repeated for each normalized intensity autocorrelation function $g_2(\tau)$ measurement, which may occur, for example, once per second.

Figure 2:
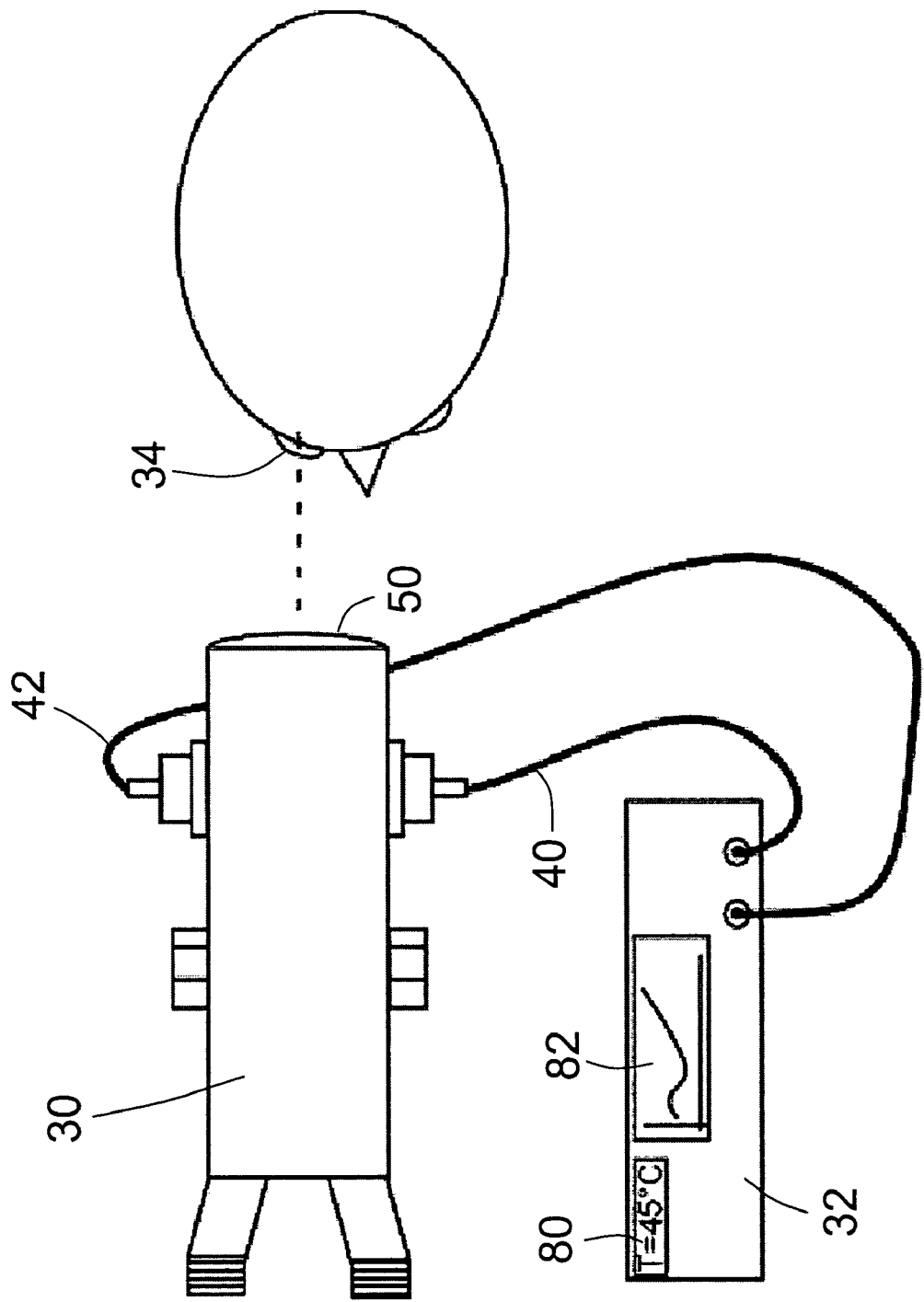
FIG. 2 diagrammatically shows a suitable measurement system for performing the retinal tissue temperature measurement of FIG. 1.

With reference to FIG. 2, a block diagram of a suitable apparatus for performing retinal temperature measurement includes a modified ophthalmic microscope 30 (for example, Haag-Streit AG, Switzerland) and a control unit 32. An ophthalmic microscope is commonly used during laser eye treatment to enable the medical operator to see the treated region of an eye 34. By modifying this instrument to produce the modified ophthalmic microscope 30 it is ensured that retinal temperature measurement is performed in the region observed and treated. The two units 30, 32 are connected by two single-mode optical fibers 40, 42.

With continuing reference to FIG. 2 and with further reference to FIGS. 3A and 3B, the modified ophthalmic microscope 30 includes an objective lens or lensing system 50. The probe beam 14 is generated by a first laser 52 disposed in the control unit 32 or elsewhere, and is guided by the single mode optical fiber 40 to a collimator 54. The resulting collimated beam is deflected by a dichroic mirror 56 and focused on the retina 10 by the microscope objective 50.

The secondary emitted beam 16 is collected by the objective lens 50, deflected by a second dichroic mirror 60, and focused into the single mode fiber 42 by a second collimator 62. The dichroic mirrors 56, 60 are designed to reflect light with the wavelength of the first laser 52, and are also designed to reflect light with a wavelength of a second laser 66 disposed in the control unit 32 or elsewhere. Light at other wavelengths is preferably substantially transmitted by the dichroic mirrors 56, 60 in order to provide an open view for the operator to see the treated retinal tissue 10 through the modified ophthalmic microscope 30. A beam stopper 70 is optionally disposed between the dichroic mirrors 56, 60 to substantially block light from passing directly from the probe beam 14 to the collection collimator 62.

With particular reference to FIG. 3B, the control unit 32 includes control/data processing electronics 72 that control the system and process the acquired data. The electronics 72 can be embodied as a personal computer, an electronics board with discrete and/or integrated electronics, an application-specific integrated circuit (ASIC), a programmed microprocessor, or the like. Constants used in the data processing, such as absorption and scattering coefficients, are stored in memory of the electronics 72 or in a separate memory unit.

Before the laser treatment commences, the system is optically aligned as follows. An optical switch 74 couples the second laser 66 with the optical fiber 42. In this switched setting, a medical operator looking through the modified ophthalmic microscope 30 sees three spots on the retina 10: (i) the alignment beam of the treatment laser 12; (ii) the probe beam 14; and (iii) a beam produced by the second laser 66 along the path from which the secondary emission 16 is collected. The correct focus position can be determined using a graduated concentric grind on the ocular of the microscope 30 in order to select a distance p between the position of the probe beam 14 and the collection point. When the right region is located using a pedal switch the medical operator starts the procedure.

After optical alignment but before beginning the laser treatment, the optical switch 74 is switched to couple the secondary emitted fiber 42 to a single photon counting detector (SPCM) 76, and the calibration process for determining the calibration constant $K_{cal}$ is performed. A digital correlator 78 performs the signal correlation for measuring the normalized intensity autocorrelation function $g_2(\tau)$ with the eye 34 substantially at normal body temperature (typically about 37° C.), and the control/data processing electronics 72 computes the electric field autocorrelation $G_1$ based on the autocorrelation function $g_2(\tau)$, optimizes the $k_D$ value with respect to autocorrelation $G_1$, and computes the calibration constant $K_{cal}$ from $k_{D1}$.

After the calibration, the treatment laser beam 12 is applied, which begins to heat up the treatment area of retinal tissue 10. The retinal temperature measurement process is performed periodically during the laser treatment, for example once per second. For each retinal temperature measurement cycle, the SPCM 76 and digital correlator 78, in conjunction with the control/data processing electronics 72, perform measurement of the normalized intensity autocorrelation function $g_2(\tau)$. The control/data processing electronics 72 computes the electric field autocorrelation $G_1$ based on the autocorrelation function $g_2(\tau)$, optimizes the $k_D$ value with respect to autocorrelation $G_1$, and computes the retinal temperature from $k_{D1}$ and the previously determined calibration constant Kcal.

In some embodiments, the control unit 32 includes a numeric display 80 that displays the measured retinal temperature value. In some embodiments, the control unit 32 includes a graphical display 82 that plots retinal temperature as a function of time. In some embodiments, both numeric and graphical displays 80, 82 are provided. Using one or both readout displays 80, 82, the medical operation can stop the procedure when the desired retinal temperature is reached. In another approach, a feedback loop or threshold detector can be incorporated into the control/data processing electronics 72 to terminate the laser treatment when the retinal tissue temperature reaches a threshold value, a time-integrated temperature value, or other stopping criterion. In some embodiments, the medical operator ordinarily stops the procedure manually when the displays 80, 82 indicate the desired retinal temperature has been reached, but automated threshold or feedback loop incorporated into the control/data processing electronics 72 provides backup safety interlocking that prevents overexposure of the treated retinal tissue 10.

Those skilled in the art will appreciate that the retinal temperature measurements disclosed herein have certain advantages. The retinal temperature measurements disclosed herein directly measure the temperature of the retinal region at the treatment position. The retinal temperature measurements disclosed herein are non-contact and non-invasive measurements that do not harm the patient. The retinal temperature measurements disclosed herein are readily integrated into standard instrumentation used in ophthalmology. The retinal temperature measurements disclosed herein are individually pre-calibrated for each retinal region under treatment through determination of the calibration constant $K_{cal}$. Implementation of the retinal temperature measurements disclosed herein are generally also relatively inexpensive.

The disclosed retinal temperature measurement methods have been performed in-vitro on the retina of enucleated bovine eyes. Two bovine eyes were obtained from the local slaughterhouse three hours after death and packed on ice during the delivery. The eyes were cut with a razor blade a few millimeters anterior to and parallel to the equator of the globe. The incision was extended completely around the globe with a scissors or a razor blade. The anterior and posterior halves of the eye were gently separated. Care was taken to keep the retina in its natural position, since it can detach during such preparations. Some of the vitreous remained connected to the retina.

Figure 4:
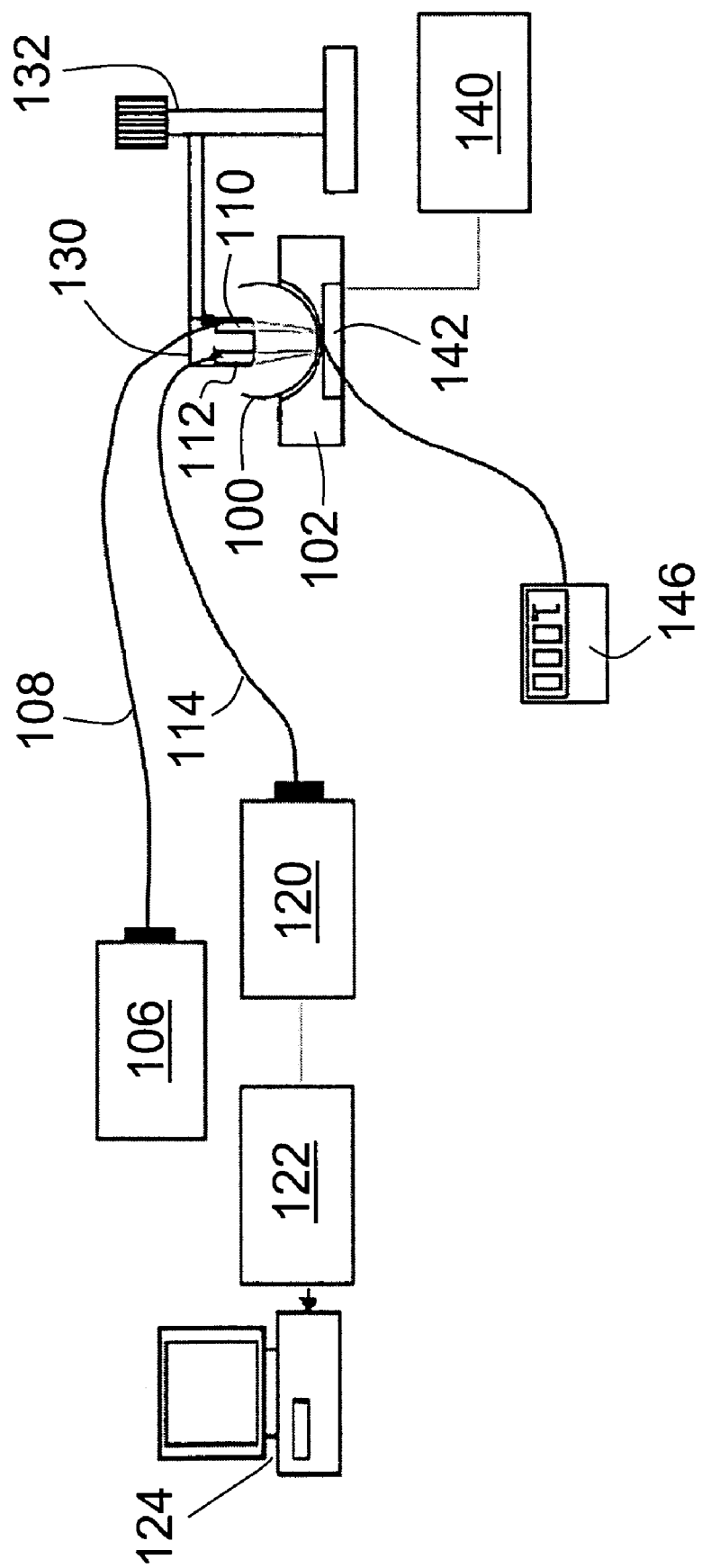
FIG. 4 diagrammatically shows a measurement system used to perform in-vitro measurements of retinal temperature of bovine retinas using the measurement method of FIG. 1.

With reference to FIG. 4, the posterior half of the eye including retinal tissue 100 was placed into a semispherical holder 102 designed to fit the shape of the bovine eyes. The retinal tissue 100 was submitted for examination and a measuring position in the central retina close to the fovea was chosen. A helium-neon (HeNe) laser 106 was coupled to a single-mode fiber 108. The light at the output of the fiber 108 was focused on the retinal tissue 100 by a gradient index (GRIN) lens 110. Collection of secondary emitted radiation was performed by a second GRIN lens 112 that focuses the light into a second single-mode fiber 114. This second fiber 114 was connected to a single photon counting module (SPCM) 120. The electrical signal from the SPCM 120 was processed by a digital correlator 122 plugged in a computer 124. The two GRIN lenses 110, 112 were fixed into a steel cylinder 130 that, during the measurement, was inserted into the vitreous humor connected to the retina. Using a microtranslator 132 the position of the steel cylinder 130 was adjusted to fix at 0.25 millimeters a distance ρ between the injection of the probe beam produced by the HeNe laser 106 and the collection point. The temperature of the eye holder 102 was controlled by a thermostatic circuit 140 including a Peltier cell 142. The retinal tissue temperature was measured with a thermocouple-based digital thermometer 146 in the area of the injection of the probe beam and the collection point. At selected temperatures determined by the digital thermometer 146, the autocorrelation output of the digital correlator 122 was processed by the computer 124 generally in accordance with Equations (1)-(6) to produce values of the product $\alpha D_B$ at various temperatures.

Figure 5B:
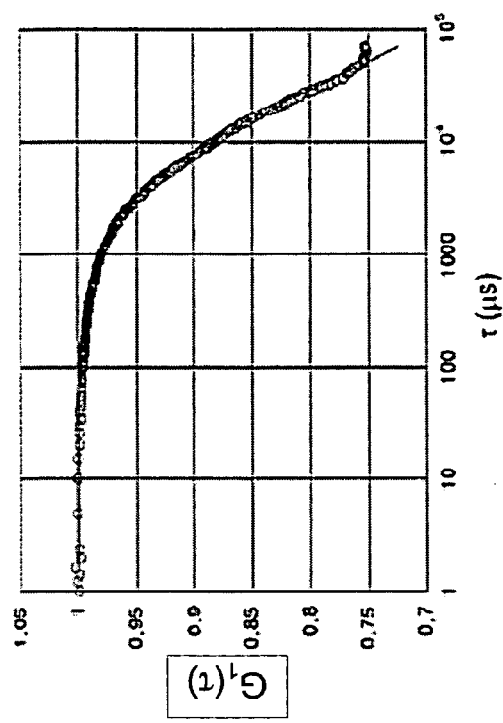
FIG. 5B shows the normalized field autocorrelation function obtained from the intensity autocorrelation function of FIG. 5A FIGS. 6A and 6B show the values of parameter $k_D$ obtained for two bovine retinal tissues, respectively, measured as a function of temperature.
Figure 5A:
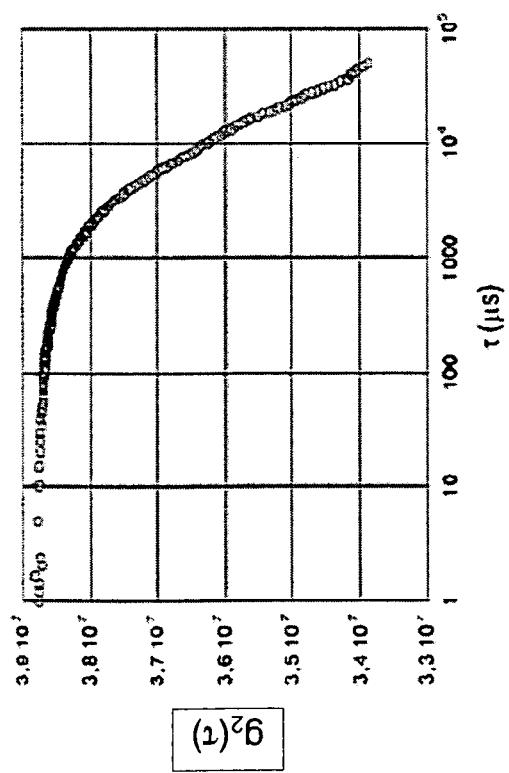
FIG. 5A shows a typical intensity autocorrelation function obtained for a cow retina using the test system of FIG. 4.

FIG. 5A shows a typical intensity autocorrelation function $g_2(\tau)$ obtained for a cow retina using the test system of FIG. 4. Solving Equation (2) for the normalized field autocorrelation function $G_1$ yields:

$$G_1(\tau) = \frac{g_2(\tau) - 1}{\beta}. \tag{7}$$

FIG. 5B shows the normalized field autocorrelation function $G_1$ obtained from the intensity autocorrelation function $g_2(\tau)$ of FIG. 5A using Equation (7). The resulting normalized field autocorrelation function $G_1$ is fitted by:

$$\text{Fit}(\tau) = h \cdot G_1(\tau) + j \tag{8},$$

where $G_1(\tau)$ is obtained from Equation (4) by fixing the following parameters: r=0.25 mm; $\mu_a$=0.01391 mm$^{-1}$; and $\mu'_s$=1.2 mm$^{-1}$. The non-linear fitting procedure was performed by commercial software (KaleidaGraph, available from Synergy Software, Reading, Pa.) that calculated the optimal values of parameter h, j and $k_D$ providing an optimized data fit. From the optimized value of $k_D$, the value of $k_{D1}$ was calculated using Equation (6).

Figures 6A, 6B:
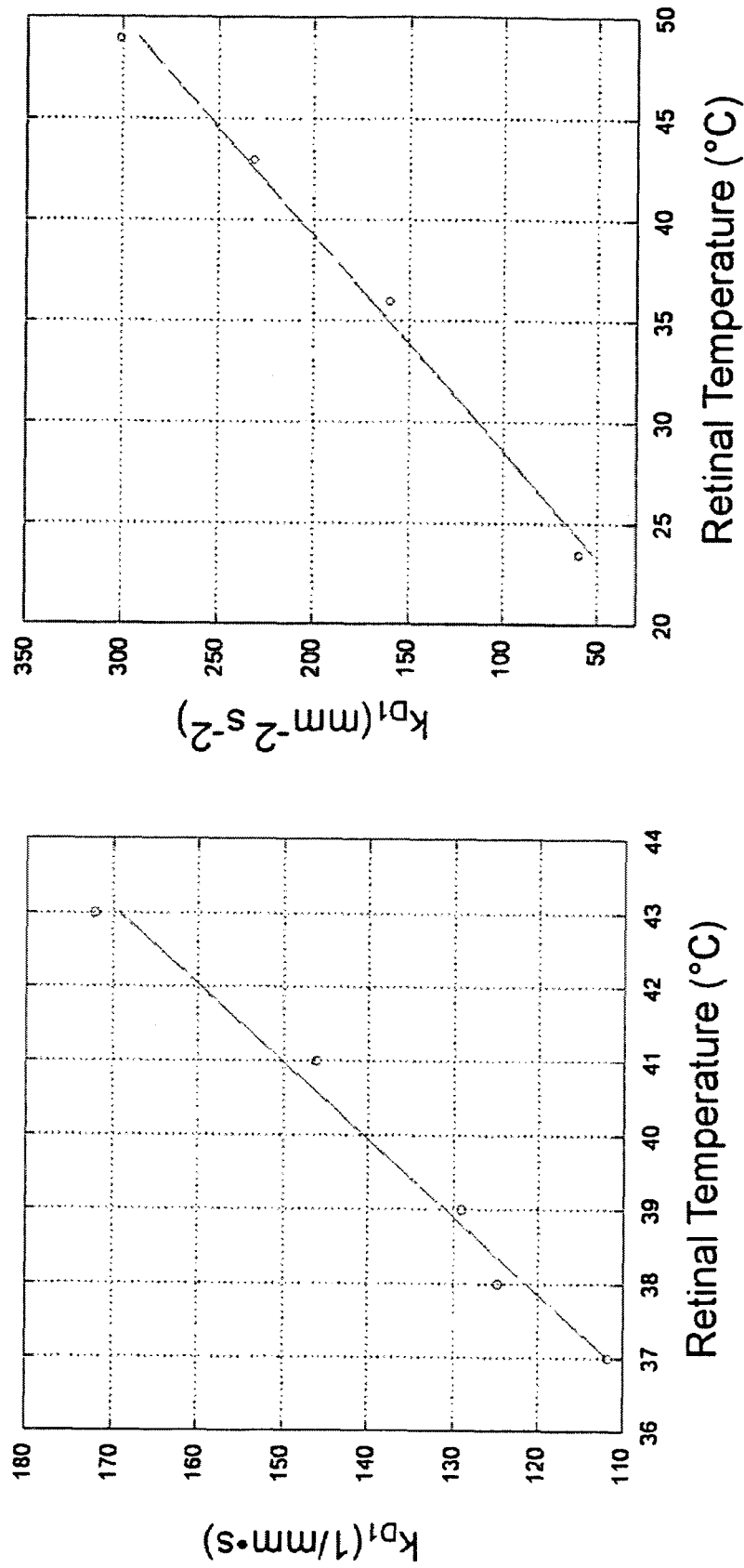

This procedure was repeated for different temperatures of the retina. FIGS. 6A and 6B show the values of $k_{D1}$ obtained for the two bovine retinal tissues, respectively, considered as a function of the sample temperature measured by the thermocouple-based digital thermometer 146. The parameter $k_{D1}$ exhibits a linear trend with respect to retinal temperature for both bovine retina samples, in accordance with the relationship $K_{cal}=k_{D1}/T$ where $K_{cal}$ is the substantially temperature-independent calibration constant. In FIGS. 6A and 6B, similar values of the slope $K_{cal}$ were obtained for the two bovine retina samples; in general, however, the calibration constant $K_{cal}$ may be sample-dependent since it has dependence upon tissue perfusion (the retinal tissues were not perfuse in the measurements shown in FIGS. 6A and 6B). Moreover, $K_{cal}$ may also depend on the measuring position. Hence, in preferred embodiments the calibration constant $K_{cal}$ is measured for each retina prior to initiating the laser treatment. Additionally, the constant $K_{cal}$ should be recalibrated whenever the treatment position is changed.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method for measuring retinal temperature, the method comprising:
generating secondary emitted light emanating from retinal tissue;
detecting the secondary emitted light emanating from the retinal tissue;
statistically analyzing temporal fluctuation of the detected secondary emitted light using a control unit including electronics configured for determining a statistical scattering characteristic of the secondary emitted light, the statistical scattering characteristic modeling substantially Brownian motion of illuminated particles of the retinal tissue, and to derive a temperature of the retinal tissue from the statistical scattering characteristic modeling substantially Brownian motion of illuminated particles of the retinal tissue.

2. The method as set forth in claim 1, wherein the statistical analyzing and deriving of a temperature of the retinal tissue from the statistical scattering characteristic comprises:
computing a parameter $k_D$ modeling substantially Brownian motion of illuminated particles of the retinal tissue, the retinal temperature being derived from the parameter $k_D$.

3. The method as set forth in claim 2, wherein the computing of the parameter $k_D$ comprises:
determining an autocorrelation of the secondary emitted light; and
fitting the autocorrelation with a model having parametric dependence upon the parameter $k_D$ of the retinal tissue.

4. The method as set forth in claim 2, wherein the deriving of the retinal temperature comprises:
determining a relationship between the retinal temperature and the parameter $k_D$.

5. The method as set forth in claim 4, wherein the relationship between the retinal temperature and the parameter $k_D$ is a linear relationship.

6. The method as set forth in claim 1, wherein the determining of a statistical scattering characteristic comprises:
determining an autocorrelation of the secondary emitted light, the statistical scattering characteristic modeling substantially Brownian motion of illuminated particles of the retinal tissue being derived from the autocorrelation.

7. The method as set forth in claim 6, wherein the deriving of the retinal temperature from the statistical scattering characteristic comprises:
deriving the retinal temperature based on a linear relationship between the statistical scattering characteristic modeling substantially Brownian motion of illuminated particles of the retinal tissue and the retinal temperature.

8. A laser eye treatment method comprising:
applying a treatment laser to a treatment area of retinal tissue;
generating secondary emitted light emanating from the treatment area of retinal tissue;
detecting the secondary emitted light; and
processing the detected secondary emitted light using a control system including electronics configured to perform method operations including determining a statistical scattering characteristic of the secondary emitted light computing a parameter $k_D$ of molecules of the treatment area of retinal tissue from the statistical scattering characteristic, and deriving a retinal temperature from the parameter $k_D$.

9. The laser eye treatment method as set forth in claim 8, wherein the determining of a statistical scattering characteristic comprises:
   determining an autocorrelation of the secondary emitted light.

10. The laser eye treatment method as set forth in claim 9, wherein the computing of a parameter $k_D$ comprises:
   fitting the autocorrelation with a model having parametric dependence upon the parameter $k_D$ of the retinal tissue.

11. The laser eye treatment method as set forth in claim 9, wherein the deriving of a retinal temperature from the parameter $k_D$ comprises:
   determining a constant of proportionality between the retinal temperature and the parameter $k_D$.

12. The laser eye treatment method as set forth in claim 11, wherein the determining of a constant of proportionality comprises:
   performing the generating of secondary emitted light, the determining of a statistical scattering characteristic, and the computing a parameter $k_D$ at normal body temperature;
   deriving the constant of proportionality based on (i) the parameter $k_D$ at normal body temperature and (ii) the normal body temperature.

13. The laser eye treatment method as set forth in claim 9, wherein the deriving of a retinal temperature from the parameter $k_D$ comprises:
   determining an intercept of a linear relation between the retinal temperature and the parameter $k_D$.

14. The A laser eye treatment apparatus comprising:
   a continuous wave probe light source for generating secondary light emanating from a treatment area of retinal tissue that is irradiated by a treatment light source;
   an optical detector for detecting the secondary light and
   a processor for statistically analyzing the secondary light to determine a temperature of the treatment area of retinal tissue, the processor including a correlator that generates an autocorrelation of the output of the optical detector.

15. The laser eye treatment apparatus as set forth in claim 14, further comprising:
   a treatment light source for generating lesions in the treatment area of retinal tissue.

16. The laser eye treatment apparatus as set forth in claim 14, wherein the continuous wave probe light source for generating secondary emitted light also functions as a treatment light source for generating lesions in the treatment area of retinal tissue.

17. The laser eye treatment apparatus as set forth in claim 14, wherein the processor further comprises:
   an optimizer that optimizes the autocorrelation output by the correlator with respect to a parameter $k_D$; and
   a converter that converts the parameter $k_D$ into a retinal temperature.

18. The laser eye treatment apparatus as set forth in claim 14, wherein the continuous wave probe light source is selected from a group consisting of a light emitting diode (LED) or a laser.

* * * * *